US008067005B1

(12) United States Patent (10) Patent No.: US 8,067,005 B1
Chapman et al. (45) Date of Patent: Nov. 29, 2011

(54) DIVALENT ANTIBODY FRAGMENTS

(75) Inventors: Andrew Paul Chapman, Middlesex (GB); David John King, Foster City, CA (US)

(73) Assignee: UCB Pharma S.A., Brussels (BE)

( * ) Notice: Subject to any disclaimer, the term of this patent is extended or adjusted under 35 U.S.C. 154(b) by 0 days.

(21) Appl. No.: 09/719,045

(22) PCT Filed: Jun. 8, 1999

(86) PCT No.: PCT/GB99/01800
§ 371 (c)(1),
(2), (4) Date: Dec. 7, 2000

(87) PCT Pub. No.: WO99/64460
PCT Pub. Date: Dec. 16, 1999

(30) Foreign Application Priority Data

Jun. 10, 1998 (GB) .................................. 9812545.3

(51) Int. Cl.
*A61K 39/395* (2006.01)
*C07K 16/00* (2006.01)
(52) U.S. Cl. ............... 424/178.1; 424/136.1; 424/179.1; 424/809; 530/387.3; 530/391.1; 530/866
(58) Field of Classification Search ............... 424/130.1, 424/133.1, 152.1, 172.1, 178.1; 436/809, 436/512; 530/387.1, 387.3, 388.2, 389.7, 530/391.1, 866
See application file for complete search history.

(56) References Cited

U.S. PATENT DOCUMENTS

| | | | |
|---|---|---|---|
| 5,436,154 A * | 7/1995 | Barbanti et al. | 435/240.27 |
| 5,534,254 A * | 7/1996 | Huston et al. | 424/135.1 |
| 5,968,009 A * | 10/1999 | Akita et al. | 424/141.1 |
| 6,025,158 A * | 2/2000 | Gonzalez et al. | 435/69.1 |

FOREIGN PATENT DOCUMENTS

| | | |
|---|---|---|
| EP | 0 384624 | 8/1990 |
| EP | 0 392745 | 10/1990 |
| EP | 0 348442 | 1/1993 |
| WO | WO 86/01533 | 3/1986 |
| WO | WO 89/01476 | 2/1989 |
| WO | WO 89/01974 | 3/1989 |
| WO | WO 90/09195 | 8/1990 |
| WO | WO 91/09967 | 7/1991 |
| WO | WO 92/22583 | 12/1992 |
| WO | WO 93/06231 | 4/1993 |
| WO | WO 98/25971 | 6/1998 |
| ZA | 85/8794 | 11/1985 |
| ZA | 88/8127 | 10/1988 |
| ZA | 90/2839 | 4/1990 |

OTHER PUBLICATIONS

Abuchowski, A. et al., *J. Biol. Chem*, "Alteration of Immunological Properties of Bovine Serum Albumin by Covalent Attachment of Polyethylene Glycol ",1977, 252,11, 3578-3581, "Effect of Covalent Attachment of Polyethylene Glycol on Immunogenicity and Circulating Life of Bovine Liver Catalase",3582-3586.

Benhar, I. et al., "Mutations of two lysine residues in the CDR loops of a recombinant immunotoxin that reduce its sensitivity to chemical derivatization", *Bioconjugate Chemistry*, 1994, 5, 321-326.

Chiswell, D.J. et al., Phage antibodies: will new "coliclonal" antibodies replace monoclonal antibodies? , *J. Tibtech*, 1992, 10, 80-84.

Delgado, C. et al., "Enhanced tumour specificity of an anti-carcinoembrionic antigen Fab' fragment by poly(ethylene glycol) (PEG) modification", *British. Journal of. Cancer*, 1996, 73, 175-182.

Goodson, R.J.et al., "Site-directed pegylation of recombinant interleukin-2 at its glycosylation site", *Bio/Technology*, 1990, 8, 343-346.

Hershfield, M.S. et al., "Use of site-directed mutagenesis to enhance the epitope-shielding effect of covalent modification of proteins with polyethylene glycol", *P.N.A.S.*, 1991, 88, 7185-7189.

Kitamura, K. et al., "Chemical engineering of the monoclonal antibody A7 by polyethylene Glycol for targeting cancer chemotherapy", *Cancer Res.* 1991, 51, 4310-4315.

Kramer, W. et al., "The gapped duplex DNA approach to oligonucleotide-directed mutation construction", *Nucl. Acids. Res.* 1984, 12, 9441-9457.

Ling, T.G.I. et al., "A general study of the binding and Separation in partition affinity ligand assay. Immunoassay of β2- Microglobulin", *J. Immunol. Meth*, 1983, 59, 327-337.

Lyons, A.et al., "Site-specific attachment to recombinant antibodies via introduced surface cysteine residues", *Protein Engineering.*, 1990, 3(8), 703-709.

Nucci, M. L. et al., "The therapeutic value of poly(ethylene glycol)-modified proteins", *Advanced . Drug Delivery Reviews*, 1991, 6, 133-151. Pedley, R.B. et al. "The potential for enhanced tumour localisation by poly(ethylene glycol) modification of anti-CEA antibody", *Br. J. Cancer*, 1994, 70, 1126-1130.

Stability of Protein Pharmaceuticals: in vivo Pathways of Degradation and Strategies for Protein Stabilization, 1991, 235-263, (Ahern, T.J. and Manning, M., eds. Plenum, N.Y.

Wilkinson, I, et al., "Tolerogenic polyethylene glycol derivatives of xenogeneic monoclonal immunoglobulins", *Immunol. Letters*, 1987, 15, 17-22.

Zalipsky, S. et al., "Use of functionalized ploy(Ethylene Glycol)s for modification of polypeptides", *Chemistry: Biotechnical and Biomedical Applications*, 1992, 347-370.

* cited by examiner

*Primary Examiner* — David A. Saunders
(74) *Attorney, Agent, or Firm* — Cozen O'Connor

(57) ABSTRACT

Divalent antibody fragments are described, each of which has one or more interchain bridges containing a synthetic or naturally occurring polymer selected from a polyalkylene, polyakenylene, polyoxyalkylene or polysaccharide. Each bridge may be the residue of a homo- or heterobifunctional cross-linking reagent and serves to link two heavy chains in each antibody fragment via the sulphur atoms of cysteine residues present in the chains. Each fragment may be attached to one or more effector or reporter molecules, and is of use in therapy or diagnostics where it has markedly improved binding and/or pharmacokinetic properties when compared to other antibody fragments which have the same number and type of polymer molecules but in which the polymer molecules are randomly attached.

15 Claims, 9 Drawing Sheets

Non-Reducing
1. Molecular weight marker proteins
2. Fab' and DFM mix
3. Purified DFM-PEG (10kDa SS linker)
4. Purified DFM-PEG (20kDa SS linker)
5. Purified DFM-PEG (40kDa)

Reducing
6. Fab' and DFM mix
7. Purified DFM-PEG (10kDa SS linker)
8. Purified DFM-PEG (20kDa SS linker)
9. Purified DFM-PEG (40kDa)

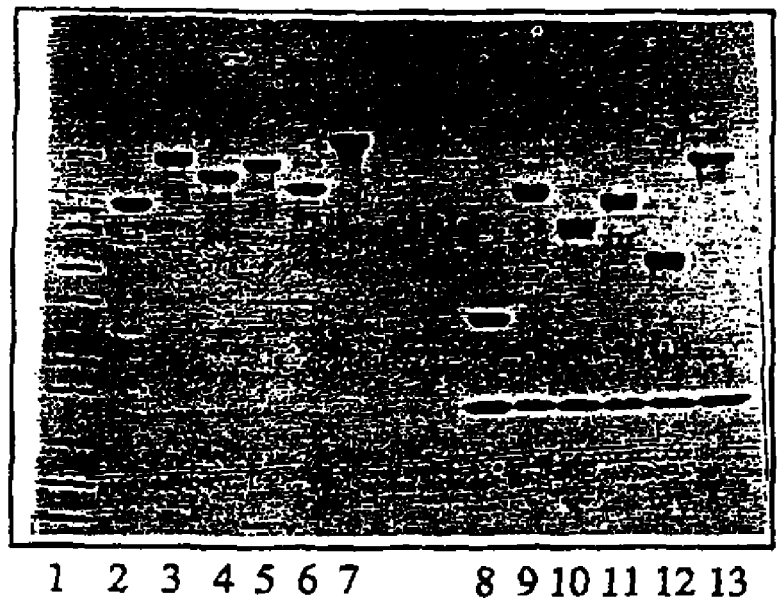

Non-Reducing
1. Molecular weight marker proteins
2. Purified DFM
3. Purified DFM-PEG (20kDa NHS linker)
4. Purified DFM-PEG (10kDa NHS linker)
5. Purified DFM-PEG (20kDa SPA linker)
6. Purified DFM-PEG (5kDa SCM linker)
7. Purified DFM-PEG (40kDa NHS linker)

Reducing
8. Purified DFM
9. Purified DFM-PEG (20kDa NHS linker)
10. Purified DFM-PEG (10kDa NHS linker)
11. Purified DFM-PEG (20kDa SPA linker)
12. Purified DFM-PEG (5kDa SCM linker)
13. Purified DFM-PEG (40kDa NHS linker)

FIGURE 6

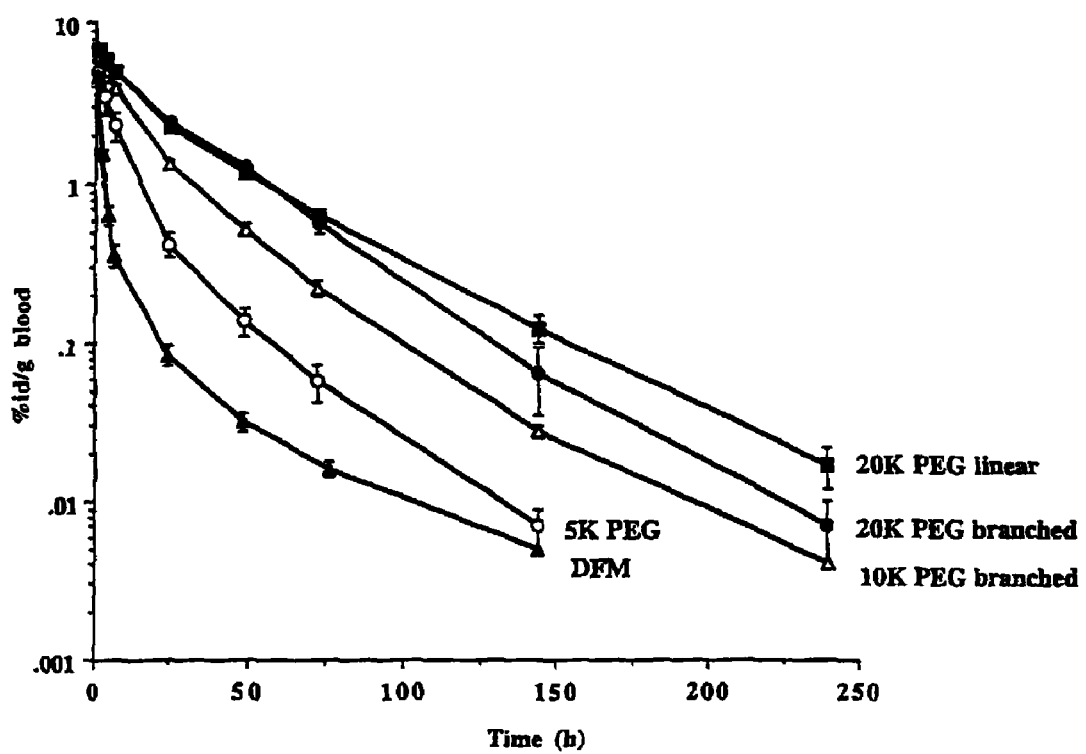
FIUGURE 7

1  2  3        4  5

Non-Reducing
1. Molecular weight marker proteins
2. DFM
3. DFM-PEG (40kDa, site-specific)

Reducing
4. DFM
5. DFM-PEG (40kDa, site-specific)

DIVALENT ANTIBODY FRAGMENTS

This invention relates to modified divalent antibody fragments, to processes for their preparation, to compositions containing them and to their use in medicine.

Antibodies are increasingly being used in the clinic for diagnostic and therapeutic purposes. The aim in each case is to exploit the combination of high specificity and affinity of the antibody-antigen interaction, to enable detection and/or treatment of a particular lesion. The antibody is used alone, or is loaded with another atom or molecule such as a radioisotope or cytotoxic drug.

The pharmacokinetics and biodistribution of an antibody play a major role in determining whether its use in the clinic will be successful. Thus the antibody must be capable of being delivered to the site of action and be retained there for a length of time suitable to achieve its purpose. It also should be present only at sub-toxic levels outside of the target and it must be catabolised in a well-defined manner.

For many uses the pharmacokinetics of antibodies are not ideal. This is especially true for tumour diagnosis and therapy with antibody-radioisotope or drug conjugates. For diagnosis with such conjugates long half-lives limit the tumour-to-background ratio and hence the sensitivity of lesion detection. For therapy, a long half-life leads to long-term exposure of normal tissues to the antibody conjugate and hence to dose-limiting toxicity.

A number of approaches are available to manipulate the pharmacokinetics of antibodies, and these usually also affect their biodistribution. The simplest and most generally applicable approach is the use of antibody fragments. These are cleared more rapidly from the circulation than whole antibodies and distribute more rapidly from the blood to the tissues, which is a particular advantage in some applications, for example for tumour imaging and therapy.

In order to improve the pharmocokinetics of antibody fragments still further we have investigated the use of polymers. The attachment of polymeric materials such as polyethylene glycol (PEG), to protein molecules is well established and it has been demonstrated that attachment of a polymer can substantially alter the pharmacological properties of a protein molecule. For example, PEG modification of proteins can alter the in vivo circulating half-life of the protein, antigenicity and immunogenicity, solubility, mechanical stability and resistance to proteolysis [Abuchowski, A. et al J. Biol. Chem. (1977) 252, 3578-3581 and 3582-3586; Nucci, M. L. et al., Adv. Drug Delivery Reviews (1991) 6, 133-151; Francis, G. et al, Pharmaceutical Biotechnology Vol. 3. (Borchardt, R. T. ed.); and Stability of Protein Pharmaceuticals: in vivo Pathways of Degradation and Strategies for Protein Stabilization (1991) pp 235-263 (Ahern, T. J and Manning, M., ed.s) Plenum, New York].

Attachment of PEG to protein molecules has been achieved using a number of different chemical methods, most of which attach PEG to lysine residues or other amino acid residues on the surface of the protein in a random fashion [Zalipsky, S. & Lee, C. Poly(ethylene glycol) Chemistry: Biotechnical and Biomedical Applications (1992) pp 347-370 (Harris, J. M., ed), Plenum, New York]. This often leads to partial impairment of the function of the protein, for example enzymes have reduced catalytic activity [Nucci, M. L. et al ibid].

Site-specific modification of proteins to introduce sites for PEG attachment has been reported. Interleukin-2, for example, has been modified by mutagenesis to replace a threonine residue which is normally glycosylated by a cysteine to allow attachment of PEG, [Goodson, R. J. & Katre, N. V. Bio/Technology (1990) 8, 343-346]. A site which is normally glycosylated was chosen as this was thought to be capable of tolerating PEG modification without perturbation of the protein structure. In another example, the enzyme purine nucleoside phosphorylase has been modified to selectively replace arginine residues with lysines to provide in this instance up to eighteen additional potential PEG attachment sites per enzyme molecule [Hershfield, M. S. et al P.N.A.S. (1991), 88, 7185-7189]. Previous studies with antibodies and antibody fragments have used random PEG attachment via lysine residues [e.g. Ling, T. G. I. & Mattiasson, B. J. Immunol. Methods (1983), 59, 327-337; Wilkinson, I. et al Immunol. Letters (1987) 15, 17-22; Kitamura, K. et al Cancer Res. (1991), 51, 4310-4315; Delgado, C. et al Br. J. Cancer (1996), 73, 175-182] and thiolated derivatives [Pedley, R. B. et al Br. J. Cancer (1994), 70, 1126-1130]. Random attachment has often resulted in modified antibodies which are only able to bind their target antigen with reduced affinity, avidity or specificity. In one attempt to overcome this, critical lysine residues in antigen binding (CDR) loops have been replaced with arginines to allow modification with less loss in immunoreactivity [Benhar, I. et al Bioconjugate Chemistry (1994) 5, 321-326].

Specific sites in the constant and the hinge regions of antibodies can be engineered to allow site-specific linkage of a range of effector and reporter molecules [Lyons, A. et al Prot. Eng. (1990), 3, 703-709; and European Patent Specifications Nos. 348442 and 347433]. We have now determined that site-specific attachment of polymers to divalent antibody fragments can be used to avoid the loss of immunoreactivity previously associated with random attachment processes. Furthermore, fragments modified in this way have markedly improved binding and/or pharmacokinetic properties when compared to fragments which have been modified randomly with the same number and type of polymer molecules.

Thus according to one aspect of the invention we provide a divalent antibody fragment comprising two antibody heavy chains and at least one polymer molecule in covalent linkage, each heavy chain being covalently linked to the other by at least one non-disulphide interchain bridge linking the sulphur atom of a cysteine residue in one chain to the sulphur atom of a cysteine residue in the other chain, said cysteine residues being located outside of the variable region domain of each chain, characterised in that at least one non-disulphide interchain bridge contains a covalently linked polymer molecule.

The term "non-disulphide" as used herein is intended to mean that S—S bridges, e.g. of the type normally found in antibodies, are excluded. An interchain bridge of the type present in a fragment according to the invention may however still be linked to a heavy chain via a —S—S— bond as described hereinafter.

The antibody fragment of the invention will in general be capable of selectively binding to an antigen. The antigen may be any cell-associated antigen, for example a cell surface antigen such as a T-cell, endothelial cell or tumour cell marker, or it may be a soluble antigen. Particular examples of cell surface antigens include adhesion molecules, for example integrins such as β1 integrins, e.g. VLA-4, E-selectin, P-selectin or L-selectin, CD2, CD3, CD4, CD5, CD7, CD8, CD11a, CD11b, CD18, CD19, CD20, CD23, CD25, CD33, CD38, CD40, CD45, CDW52, CD69, carcinoembryonic antigen (CEA), human milk fat globulin (HMFG1 and 2), MHC Class I and MHC Class II antigens, and VEGF, and where appropriate, receptors thereof. Soluble antigens include interleukins such as IL-1, IL-2, IL-3, IL-4, IL-5, IL-6, IL-8 or IL-12, viral antigens, for example respiratory syncytial virus or cytomegalovirus antigens, immunoglobulins, such as IgE, interferons such as interferon-α, interferon-β or interferon-γ, tumour necrosis factor-α, tumour necrosis factor-13, colony stimulating factors such as G-CSF or GM-CSF, and platelet derived growth factors such as PDGF-α, and PDGF-β and where appropriate receptors thereof. Each antigen may be for example a human antigen.

Particular antibody fragments according to the invention include those which selectively bind to tumour necrosis factor-α and platelet derived growth factors and receptors thereof, especially those described in the Examples hereinafter.

In order to achieve useful antigen binding properties each heavy chain in a fragment according to the invention may be paired with a complementary antibody light chain or a fragment thereof and the invention extends to such constructs. Where desired, a heavy-light chain pair may be in covalent linkage, for example a disulphide linkage as found in naturally occurring antibodies and/or a peptide linkage as found for example in recombinant single chain antibodies.

In general each heavy chain and, when present, light chain, will have a variable region domain. The term variable region domain as used herein is intended to mean that part of a heavy or light chain which contains the antigen binding site (hereinafter a $V_H$ or $V_L$ domain). The $V_H$ or $V_L$ domain may be of any size or amino acid composition and will generally comprise at least one hypervariable amino acid sequence responsible for antigen binding embedded in a framework sequence.

Each $V_H$ or $V_L$ domain may be any naturally occurring variable domain or an engineered version thereof. By engineered version is meant a variable region domain which has been created using recombinant DNA engineering techniques. Such engineered versions include those created for example from natural antibody variable regions by insertions, deletions or changes in or to the amino acid sequences of the natural antibodies. Particular examples of this type include those engineered $V_H$ or $V_L$ domains containing at least one CDR and optionally one or more framework amino acids from one antibody and the remainder of the variable region domain from a second antibody.

Each $V_H$ domain will generally be covalently attached to at least one cysteine residue. The location of each cysteine residue may be varied according to the size and nature of the antibody fragment required. Thus, in one extreme example a cysteine residue may be attached directly to the C-terminal amino acid of the $V_H$ domain. This may then function as the bridging site for an interchain bridge containing a polymer molecule. Two $V_H$ domains of this type may thus be bridged to form a fragment according to the invention.

In practice however, it is generally preferable that the $V_H$ domain is covalently attached at the C-terminal amino acid to at least one other antibody domain or a fragment thereof which contains a cysteine residue. Thus, for example a $V_H$ domain may be linked to an immunoglobulin $C_H1$ domain or a fragment thereof. The CH1 domain may be extended with further amino acids, for example to provide a hinge region domain as found generally in immunoglobulins, or to provide further domains, such as antibody CH2 and CH3 domains. In each of the above cases at least one cysteine residue may be located at any point throughout any domain to form a bridging site for an interchain bridge containing a polymer molecule.

Similarly any $V_L$ domain present in a fragment according to the invention may be attached to an antibody light chain constant domain ($C_L$) or a fragment thereof.

The polymer molecule in the fragment according to the invention may in general be a synthetic or naturally occurring polymer, for example an optionally substituted straight or branched chain polyalkylene, polyalkenylene or polyoxyalkylene polymer or a branched or unbranched polysaccharide, e.g. a homo- or heteropolysaccharide.

Particular optional substituents which may be present on the above-mentioned synthetic polymers include one or more hydroxy, methyl or methoxy groups. Particular examples of synthetic polymers include optionally substituted straight or branched chain poly(ethylene glycol), poly(propylene glycol), or poly(vinyl alcohol) and derivatives thereof, especially optionally substituted poly(ethylene glycol) such as methoxy (polyethylene glycol) and derivatives thereof. Particular naturally occurring polymers include lactose, amylose, dextran or glycogen and derivatives thereof. "Derivatives" as used herein is intended to include reactive derivatives, for example active esters such as succinimidyl esters and the like. The reactive group may be linked directly or through a linker segment to the polymer. It will be appreciated that the residue of such a group will in some instances form part of the product of the invention as the linking group between the polymer and the interchain bridge.

The size of the polymer may be varied as desired, but will generally be in an average molecular weight range from around 500 Da to around 50000 Da for example from 5000 to 40000 Da and including 25000 to 40000 Da. The polymer size may in particular be selected on the basis of the intended use of the product. Thus for example where the product is intended to leave the circulation and penetrate tissue, for example for use in the treatment of a tumour, it may be advantageous to use a small molecular weight polymer, for example around 5000 Da. For applications where the product remains in the circulation it may be advantageous to use a higher molecular weight polymer, for example in the range 25000 Da to 40000 Da.

In general, each polymer molecule in the antibody fragment according to the invention forms part of an interchain bridge. Each bridge serves to link two heavy chains and in each chain will be covalently linked to a sulphur atom of a cysteine residue. The covalent linkage will generally be a disulphide bond or, in particular a sulphur-carbon bond.

Each interchain bridge may in general be of any desired length or composition. Suitable bridges include residues of homo- or heterofunctional cross-linking reagents, particularly homo- or heterobifunctional cross-linking reagents containing one or more covalently linked polymer molecules as just described.

Homo- or heterofunctional cross-linking reagents include polyvalent, especially bivalent radicals of aliphatic, heteroaliphatic, cycloaliphatic, heterocycloaliphatic, aromatic or heteroaromatic groups containing two thiol reactive functional groups. Each fragment according to the invention will have an interchain bridge derived from such a reagent in which each thiol reactive functional group is in covalent linkage with a sulphur atom of a cysteine residue. Particular thiol reactive functional groups include α-halocarboxylic acids or esters, e.g. iodoacetamide, imides, e.g. maleimide, vinyl sulphones or disulphides.

Particular bridges include optionally substituted straight or branched $C_{4-20}$ alkylene, $C_{4-20}$alkenylene or $C_{4-20}$alkynylene chains optionally interrupted by one or more heteroatoms or heteroatom-containing groups such as —O— or —S— atoms or —N($R^1$)— [where $R^1$ is a hydrogen atom or a $C_{1-6}$alkyl group], —CON($R^1$)—, —N($R^1$)CO—, —SO$_2$N($R^1$)—, —N($R^1$)SO$_2$—, —C(O)—, —S(O)—, —S(O)$_2$—, —OCON($R^1$)—, —N($R^1$)C(O)O—, —C(O)O— groups, or by cyclopentylene, cyclohexylene, phenylene or substituted phenylene groups. Optional substituents include for example one or more amino or substituted amino groups, e.g. —N(R$^1$)$_2$ groups where each R$^1$ atom or group may be the same or different.

The polymer may be covalently attached at any location in the interchain bridge, generally through a heteroatom or heteroatom-containing group as just described in relation to particular interchain bridges.

Particularly useful fragments according to the invention are those containing a single interchain bridge. In these particular fragments the polymer may especially be a synthetic polymer, particularly a polyalkylene polymer such as poly(ethylene glycol) or especially methoxypoly(ethylene glycol) or a derivative thereof, and especially with a molecular weight in the range from about 25000 Da to about 40000 Da. The bridge may in particular be an optionally substituted straight or branched C$_{4-20}$alkylene chain optionally interrupted by one or more heteroatoms or heteroatom-containing groups as described previously.

Each heavy chain in the fragments according to the invention is preferably a V$_H$-CH1 chain terminally substituted by a hinge region domain, for example as naturally found in immunoglobulins. Each chain is preferably paired with a light chain, particularly a V$_H$-C$_L$ chain, thus for example forming a Fab' fragment. In preferred fragments of the invention containing heavy or heavy-light chain pairs of these types a single interchain bridge will be present, particularly bridging a cysteine residue located in the hinge sequence of each heavy chain. Desirably this will be the only cysteine residue present in each hinge sequence.

Where desired, the antibody fragment according to the invention may additionally have one or more effector or reporter molecules attached to it and the invention extends to such modified antibodies. The effector or reporter molecules may be attached to the antibody fragment through any available amino acid side-chain or terminal amino acid functional group located in the fragment, for example any free amino, imino, hydroxyl or carboxyl group.

Effector molecules include, for example, antineoplastic agents, toxins (such as enzymatically active toxins of bacterial or plant origin and fragments thereof e.g. ricin and fragments thereof) biologically active proteins, for example enzymes, nucleic acids and fragments thereof, e.g. DNA, RNA and fragments thereof, radionuclides, particularly radioiodide, and chelated metals. Suitable reporter groups include chelated metals, fluorescent compounds or compounds which may be detected by NMR or ESR spectroscopy.

Particular antineoplastic agents include cytotoxic and cytostatic agents, for example alkylating agents, such as nitrogen mustards (e.g. chlorambucil, melphalan, mechlorethamine, cyclophosphamide, or uracil mustard) and derivatives thereof, triethylenephosphoramide, triethylenethiophosphor-amide, busulphan, or cisplatin; antimetabolites, such as methotrexate, fluorouracil, floxuridine, cytarabine, mercaptopurine, thioguanine, fluoroacetic acid or fluorocitric acid, antibiotics, such as bleomycins (e.g. bleomycin sulphate), doxorubicin, daunorubicin, mitomycins (e.g. mitomycin C), actinomycins (e.g. dactinomycin) plicamycin, calichaemicin and derivatives thereof, or esperamicin and derivatives thereof; mitotic inhibitors, such as etoposide, vincristine or vinblastine and derivatives thereof; alkaloids, such as ellipticine; polyols such as taxicin-I or taxicin-II; hormones, such as androgens (e.g. dromostanolone or testolactone), progestins (e.g. megestrol acetate or medroxyprogesterone acetate), estrogens (e.g. dimethylstilbestrol diphosphate, polyestradiol phosphate or estramustine phosphate) or antiestrogens (e.g. tamoxifen); anthraquinones, such as mitoxantrone, ureas, such as hydroxyurea; hydrazines, such as procarbazine; or imidazoles, such as dacarbazine.

Particularly useful effector groups are calichaemicin and derivatives thereof (see for example South African Patent Specifications Nos. 85/8794, 88/8127 and 90/2839).

Chelated metals include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd and $^{47}$Sc.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in International Patent Specification No. WO 92/22583); and polyamides, especially desferriox-amine and derivatives thereof.

The antibody fragment according to the invention may be prepared by reacting an antibody fragment containing a heavy chain reactive cysteine residue located outside of the V$_H$ domain with a thiol-selective cross-linking reagent containing a polymer as defined herein. The reaction may generally be performed in a solvent, for example an aqueous buffer solution such as an acetate or phosphate buffer, at around neutral pH, for example around pH 4.5 to around pH 8.0, at for example ambient temperature. The antibody will generally be employed in excess concentration relative to the concentration of the cross linking reagent. In some instances it may be necessary to reduce the antibody starting material with a reagent such as β-mercaptoethylamine (for example as described in Example 1 hereinafter) to generate an appropriately reactive cysteine residue. Where necessary, the desired product may be separated from any unreacted starting materials or any other unwanted product generated during the production process by conventional means, for example by chromatography.

The antibody fragment starting material may be obtained from any whole antibody, especially a whole monoclonal antibody, [prepared by conventional immunisation and cell fusion procedures], using any suitable standard enzymatic cleavage and/or digestion techniques, for example by treatment with pepsin. Alternatively, the antibody starting material may be prepared by the use of recombinant DNA techniques involving the manipulation and re-expression of DNA encoding antibody variable and/or constant regions. Such DNA is known and/or is readily available from DNA libraries including for example phage-antibody libraries [see Chiswell, D J and McCafferty, J. Tibtech. 10 80-84 (1992)] or where desired can be synthesised. Standard molecular biology and/or chemistry procedures may be used to sequence and manipulate the DNA, for example, to introduce codons to create cysteine residues, to modify, add or delete other amino acids or domains as desired.

From here, one or more replicable expression vectors containing the DNA may be prepared and used to transform an appropriate cell line, e.g. a non-producing myeloma cell line, such as a mouse NSO line or a bacterial, e.g. E. coli line, in which production of the antibody fragment will occur. In order to obtain efficient transcription and translation, the DNA sequence in each vector should include appropriate regulatory sequences, particularly a promoter and leader sequence operably linked to the variable domain sequence. Particular methods for producing antibody fragments in this way are generally well known and routinely used. For example, basic molecular biology procedures are described by Maniatis al [Molecular Cloning, Cold Spring Harbor Laboratory, New York, 1989]; DNA sequencing can be performed as described in Sanger et al [PNAS 74, 5463, (1977)] and the Amersham International plc sequencing handbook; and site directed mutagenesis can be carried out according to the method of Kramer et al [Nucl. Acids Res. 12, 9441, (1984)] and the Anglian Biotechnology Ltd handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews [ed. Tombs, M P, 10, Chapter 1, 1992, Intercept, Andover, UK] and in International Patent Specification No. WO 91/09967.

The thiol-selective cross-linking reagent for use in the preparation of antibody fragments according to the invention may be obtained by reaction of any thiol-reactive cross-linking agent (containing for example thiol reactive groups such as an $\alpha$-halocarboxylic acid or ester, e.g. iodoacetamide, an imide, e.g. maleimide, a vinyl sulphone, or a disulphide) with an appropriately functionalised polymer. Suitable polymer starting materials may be obtained commercially (for example from Shearwater Polymers Inc., Huntsville, Ala., USA) or may be prepared from commercially available starting materials using conventional chemical procedures, for example as described by Zalipsky, S & Lee, C, ibid. The reaction may in general be a conventional coupling reaction between the functionalised polymer, for example an active ester of the polymer, and an appropriate functional group, for example an amine, present in the cross-linking reagent. Standard reaction conditions may be used, for example as described in the experimental section hereinafter for coupling an active ester with an amine. Suitable cross-linking reagents are readily available from commercially available sources or may be simply synthesised using conventional procedures from commercially available materials, for example as described in European Patent Specification No. 384624 and International Patent Specification No. WO 92/22583 and the experimental section hereinafter.

Where it is desired to obtain an antibody fragment according to the invention linked to an effector or reporter molecule this may be prepared by standard chemical or recombinant DNA procedures in which the antibody fragment is linked either directly or via a coupling agent to the effector or reporter molecule either before or after reaction with the activated polymer as appropriate. Particular chemical procedures include for example those described in International Patent Specification Nos. WO 93/06231, WO 92/22583, WO 90,09195 and WO 89/01476. Alternatively, where the effector or reporter molecule is a protein or polypeptide the linkage may be achieved using recombinant DNA procedures, for example as described in International Patent Specification No. WO 86/01533 and European Patent Specification No. 392745.

The antibody fragment according to the invention may be useful in the detection or treatment of a number of diseases or disorders. Such diseases or disorders may include those described under the general headings of infectious disease, e.g. viral infection; inflammatory disease/autoimmunity e.g. rheumatoid arthritis, osteoarthritis, inflammatory bowel disease; cancer; allergic/atopic disease e.g. asthma, eczema; congenital disease, e.g. cystic fibrosis, sickle cell anaemia; dermatologic disease, e.g. psoriasis; neurologic disease, e.g. multiple sclerosis; transplants e.g. organ transplant rejection, graft-versus-host disease; and metabolic/idiopathic disease e.g. diabetes.

The antibody fragments according to the invention may be formulated for use in therapy and/or diagnosis and according to a further aspect of the invention we provide a pharmaceutical composition comprising a modified monovalent antibody fragment comprising a monovalent antibody fragment and at least one polymer molecule in covalent linkage characterised in that each covalent linkage is through a sulphur atom of a cysteine residue located in the antibody fragment outside of the variable region domain of the fragment, together with one or more pharmaceutically acceptable excipients, diluents or carriers.

As explained above, the antibody fragment in this aspect of the invention may be optionally linked to one or more effector or reporter groups.

The pharmaceutical composition may take any suitable form for administration, and, preferably is in a form suitable for parenteral administration e.g. by injection or infusion, for example by bolus injection or continuous infusion. Where the composition is for injection of infusion, it may take the form of a suspension, solution or emulsion in an oily or aqueous vehicle and it may contain formulatory agents such as suspending, preservative, stabilising and/or dispersing agents.

Alternatively, the antibody composition may be in dry form, for reconstitution before use with an appropriate sterile liquid.

If the antibody composition is suitable for oral administration the formulation may contain, in addition to the active ingredient, additives such as: starch e.g. potato, maize or wheat starch or cellulose or starch derivatives such as microcrystalline cellulose; silica; various sugars such as lactose; magnesium carbonate and/or calcium phosphate. It is desirable that, if the formulation is for oral administration it will be well tolerated by the patient's digestive system. To this end, it may be desirable to include in the formulation mucus formers and resins. It may also be desirable to improve tolerance by formulating the antibody in a capsule which is insoluble in the gastric juices. It may also be preferable to include the antibody or composition in a controlled release formulation.

If the antibody composition is suitable for rectal administration the formulation may contain a binding and/or lubricating agent; for example polymeric glycols, gelatins, cocoa-butter or other vegetable waxes or fats.

Therapeutic and diagnostic uses of fragments according to the invention typically comprise administering an effective amount of the antibody fragment to a human subject. The exact amount to be administered will vary according to the use of the antibody and on the age, sex and condition of the patient but may typically be varied from about 0.1 mg to 1000 mg for example from about 1 mg to 500 mg. The antibody may be administered as a single dose or in a continuous manner over a period of time. Doses may be repeated as appropriate. Typical doses may be for example between 0.1-50 mg/kg body weight per single therapeutic dose, particularly between 0.1-20 mg/kg body weight for a single therapeutic dose.

BRIEF DESCRIPTION OF THE FIGURES

FIG. 6 SDS-PAGE analysis under non-reducing (lanes 1-7) and reducing (lanes 8-13) conditions.

FIG. 7 Pharmacokinetics of $^{125}$I-labelled anti-PDGFβR DFM-PEG (site-specific) of different types compared to unmodified DFM in rats.

Figure 1:
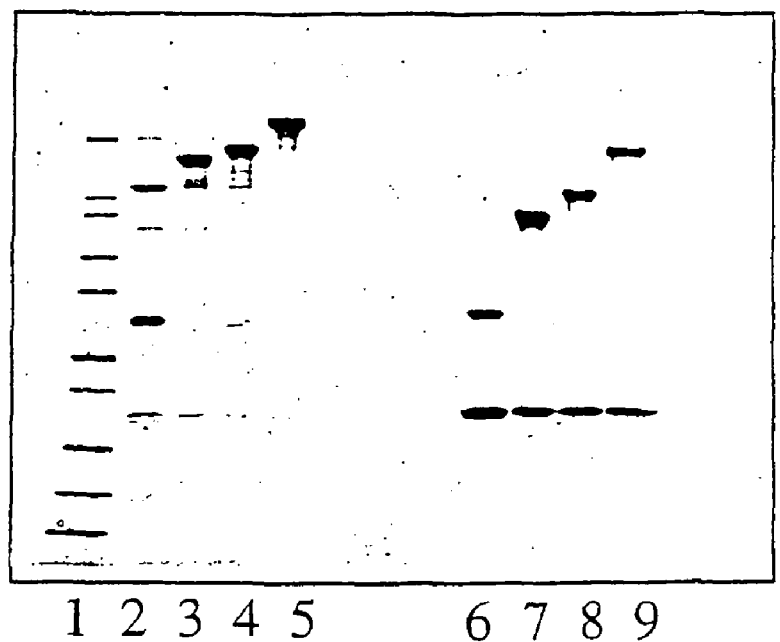
FIG. 1 SDS-PAGE analysis under non-reducing (lanes 1-5) and reducing (lanes 6-9) conditions.

The following Examples illustrate the invention.
The following abbreviations are used:

| | |
|---|---|
| PEG | $CH_3O(CH_2CH_2O)_n(CH_2)_2NHCO(CH_2)_2-$ |
| DFM- | an antibody fragment according to the invention |
| PEG | in which two Fab' fragments are cross-linked with a PEGylated dimaleimide bridge. |
| DTDP | 4,4'-dithiodipyridine |
| AUC | area under the curve |
| RT | room temperature |
| TFA | trifluoroacetic acid |
| BOC | tert butoxycarbonyl |
| CBZ | carbobenzyloxy |
| DMF | N,N-dimethylformamide |
| EDC | 1-(3-dimethylaminopropyl)-3-ethylcarbodiimide |
| BMH | bismaleimidohexane |
| PBS | phosphate buffered saline |

Preparation of Intermediate Bridging Groups
Intermediate 1

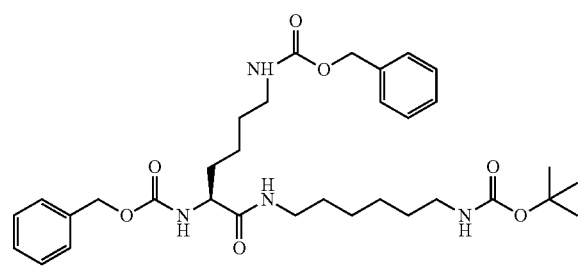

N(α)N(ε)Di-CBZ-(L)-Lysine (18.0 g, 43.3 mmol) was dissolved in anhydrous DMF (80 ml). N—BOC-1,6-diaminohexane hydrochloride (11.06, 43.75 mmol), hydroxybenzotriazole hydrate (6.43 g, 47.63 mmol), 4-methylmorpholine (5.2 ml, 47.63 mmol) and EDC (9.13 g, 47.63 mmol) were added and the mixture stirred at room temperature for 5 h. The reaction mixture was poured into $H_2O$ and extracted with ethyl acetate (4×100 ml). The combined organic layers were washed with 10% citric acid (2×50 ml), saturated $NaHCO_3$ (2×50 ml), brine (1×50 ml) and dried over $MgSO_4$. Removal of the solvent in vacuo gave Intermediate 1 (26.15 g, 100%) as a white solid. $^1$H NMR $((CD_3)_2SO)$ δ 7.79 (1H, t), 7.38-7.19 (11H, m), 6.72 ((1H, t), 5.00-4.99 (4H, m), 3.95-3.90 (1H, m), 3.08-2.87 (6H, m) and 1.60-1.05 (23H, m including 9H, s).

Intermediate 2

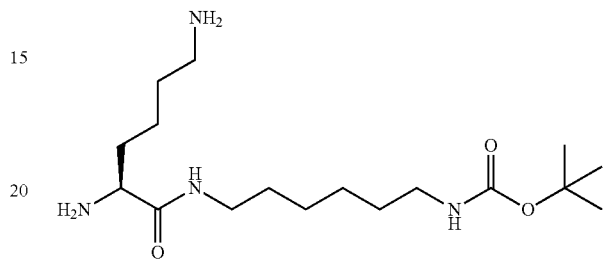

Intermediate 1 (26.15 g, 42.7 mmol) was dissolved (with warming) in ethanol (700 ml) and treated with 10% Pd/C (4.2 g). The reaction was stirred under $H_2$ gas in a hot water bath (~30°) for 4 h and then allowed to cool. $CH_2Cl_2$ (20 ml) was added and the mixture was filtered and washed well with $CH_2Cl_2$ and ethanol. Removal of the solvent in vacuo gave Intermediate 2 as an oily foam (13.8 g, 94%). $^1$H NMR $((CH_3)_2SO)$ δ 7.78 (1H, t), 3.06-2.91 (3H, m), 2.89-2.84 (4H, m), 2.52-2.43 (4H, bs) and 1.57-1.15 (23H, m. including 9H, s).

Intermediate 3

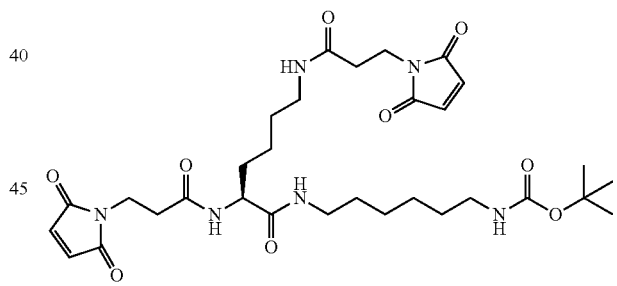

Intermediate 2 (1.47 g, 4.47 mmol) was dissolved in anhydrous DMF (25 ml) and N-succinimidyl 3-maleimidopropionate (22.38 g, 8.97 mmol) added. The reaction mixture was stirred at room temperature for 3 h. The solvent was removed in vacuo, and $CH_2Cl_2$ (50 ml) was added followed by saturated $NaHCO_3$ (50 ml). The layers were separated and the aqueous layer washed with $CH_2Cl_2$ (2×50 ml). The organic layers were combined, washed with saturated $NaHCO_3$ (2×50 ml) and dried over $MgSO_4$. The solvent was removed in vacuo, the residue treated with diethyl ether and the resulting solid filtered, washed well with diethyl ether and dried to give Intermediate 3 (2.05 g, 74%) as a white solid. $^1$H NMR $((CD_3)_2SO)$ δ 8.05 (1H, d), 7.75 (1H, t), 6.98 (4H, s), 6.72 (1H, b t), 4.21-4.07 (1H, m), 3.62 (4H, t), 3.12-2.81 (8H, m), 2.41 (2H, t) and 1.55-1.05 (23H, m, including 9H, s). Mass Spec. ES+ve 669 (MNa$^+$, 100%), 6.47 (MH$^+$, 20%), 547 (MH$^+$, $-C_5H_8O_2$, 15%.

Intermediate 4

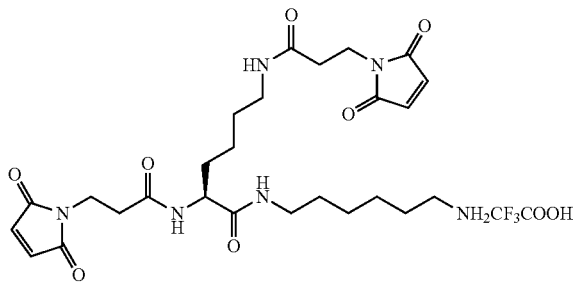

Intermediate 3 (0.3 g, 0.46 mmol) was dissolved in a 1:1 mixture of $CH_2Cl_2$/TFA (10 ml) and stirred at room temperature for 345 min. The solvent was removed in vacuo and the residue azeotroped with toluene (3×5 ml). Ethyl acetate was added to give a solid which was filtered, washed well with ethyl acetate then diethyl ether and dried in vacuo to give Intermediate 4 as a white solid (0.21 g, 68%). $^1$H NMR $(CD_3)_2SO)$ δ 8.03 (1H, d0, 7.90 (1H, t), 7.80 (1H, t), 7.69 (2H, b s), 6.99 (4H, s), 4.09 (1H, m), 3.58 (4H, t), 3.33 (HOD), 3.10-2.93 (4H, m), 2.76 (2H, b m), 2.41-2.27 (4H, m) and 1.51-1.00 (14H, m).

EXAMPLE 1

Preparation of PEGylated (40 KDa) Bridging Group

To Intermediate 4 in DMF was added one molar equivalent of N-methyl morpholine and a five-fold molar excess of amine-reactive PEG (40 kDa PEG-NHS ester; Shearwater Polymers Inc. Huntsville, Ala., USA). The mixture was incubated at RT for 2 hours with occasional agitation. Unreacted PEG was quenched with a 100-fold molar excess of glycine over PEG, added from a stock solution of 1M glycine in 0.1M phosphate buffer, pH6.0 containing 2 mM EDTA, and the mixture incubated for a minimum of a further 10 minutes to obtain the desired PEGylated bridging group.

Preparation of Fab'

Fab' from the engineered human antibody g162, which recognises human PDGF β receptor, (hereinafter PDGFβR) was expressed in *E. coli* as described in International Patent Application No. PCT/GB97/03400. The Fab' fragment has a single cysteine residue present in its hinge region available for cross-linking. Cells were harvested from fermentation culture by centrifugation and Fab' extracted by resuspending cells in 100 mM tris pH7.4 containing 10 mM EDTA and incubating at 60oC overnight. Fab' was then purified by expanded bed chromatography using a column of Streamline ATM (Pharmacia) which was pre-equilibrated with 1M glycine/glycinate pH8.0. The sample was made 1M with respect to glycine and the pH adjusted to 7.5 with 50% (w/v) sodium glycinate before application to the column in expanded bed mode. After washing with equilibration buffer, the column material was packed into a packed bed and Fab' was eluted with 0.1M citrate pH3.0.

Further purification was achieved by adjusting the pH of the eluate to 7.5 with 2M tris and applying to a column of Protein G sepharose pre-equilibrated with phosphate buffered saline pH7.4. After washing with equilibration buffer, Fab' was eluted with 0.1M glycine-HCl pH2.7. The pH of the eluted Fab' was then adjusted to 6.0 with 2M tris.

Preparation of Anti-PDGFβR DFM-PEG (Site-Specific)

Purified anti-PDGFβR Fab' was diafiltered into 0.1M phosphate buffer, pH6.0 containing 2 mM EDTA. The hinge thiol was activated by reduction with β-mercaptoethylamine. Fab' was incubated with 5 mM II-mercaptoethylamine in 0.1M phosphate buffer, pH6.0 containing 2 mM EDTA for 30 minutes at 37°. The sample was then desalted into 0.1M phosphate buffer, pH6.0 containing 2 mM EDTA, using Sephadex G-25. (PD10) columns. The number of thiol groups per Fab' molecule was measured by titration with DTDP as previously described [Lyons et a/(1990), ibid]. The Fab' was cross-linked with the PEGylated cross-linker prepared from Intermediate 4 at a Fab':linker molar ratio of 2.2:1, at 37°. The cross-linker was added in 5 aliquots at 5 minute intervals, and the sample incubated for >1 h.

The desired DFM-PEG was purified by gel filtration chromatography using Sephacryl S-400 HR (to remove unreacted Fab') in 50 mM acetate buffer pH4.5, followed by cation exchange chromatography using Mono S to separate DFM-PEG from DFM and Fab'-PEG. Mono S chromatography was carried out using a column equilibrated with 50 mM acetate pH 4.5, after application of sample and washing with equilibration buffer, bound material was eluted using a linear gradient of sodium chloride. Purified material was examined on SDS-PAGE and shown to have a slower mobility than unmodified DFM or Fab' demonstrating successful conjugation of PEG (FIG. 1).

Preparation of Randomly PEGylated anti-PDGFβR DFM-PEG

For comparative purposes anti-PDGFβR DFM was prepared and derivatised with PEG randomly. Anti-PDGFβR Fab' was reduced as described above. The Fab' was cross-linked with BMH dissolved in DMF at a Fab':BMH molar ratio of 2.2:1, at 37°. The cross-linker was added in 5 aliquots at 5 minute intervals, and the sample incubated for >1 h. The resulting DFM (diFab' cross-linked with BMH) was purified from unreacted Fab' by hydrophobic interaction chromatography using phenyl Sepharose HP.

The purified DFM was buffer-exchanged into 0.1M phosphate pH8.0 containing 2 mM EDTA. Thiols were introduced randomly onto lysine residues by reaction with a 4-fold molar excess of 2-iminothiolane (Traut's reagent) for 1 h at RT. After desalting into 0.1M phosphate pH6.0 containing 2 mM EDTA using a PD10 column, the number of thiol groups introduced was determined using titration with DTDP. The thiolated DFM was then reacted with a 3.5-fold molar excess of PEG-maleimide (Shearwater Polymers Inc, ibid) over thiols for three hours. An average of 1.3 PEG molecules were attached per DFM as quantified by gel-filtration HPLC analysis. The PEG-DFM was purified by cation exchange chromatography using Mono S. Mono S chromatography was carried out using a column equilibrated with 50 mM acetate pH 4.5, after application of sample and washing with equilibration buffer, bound material was eluted using a linear gradient of sodium chloride.

Antigen Binding Analysis by BIAcore

Kinetic analysis to determine the on and off rates for anti-PDGFβR DFM-PEG binding to PDGFβR was performed using a BIACORE 2000 (Biacore AB). The assay involves capture of a mIgG Fc-PDGFβR fusion molecule by an anti-mouse IgG, which is immobilised on the sensor chip surface, followed by an injection of anti-PDGFβR DFM-PEG. Affinipure F(ab')2 fragment of goat anti-mouse Ig, Fc fragment specific (Jackson ImmunoResearch) was immobilised on a Sensor Chip CM5 via amine coupling chemistry to a level of 11500RU. A blank surface was prepared by following the immobilisation procedure but omitting injection of the capturing molecule. HBS buffer (10 mM HEPES pH7.4, 0.15M NaCl, 3 mM EDTA, 0.005% Surfactant P20, Biacore AB) was used as the running buffer with a flow rate of 10 ml/min. An injection of mIgG Fc-PDGFβR from COS cell supernatant was captured by the immobilised anti-mouse IgG to a level between 200-250RU. Anti-PDGFβR DFM-PEG molecules were titrated over the captured mIgG Fc-PDGFβR surface from 2 mg/ml to 0.52 mg/ml. Surfaces were regenerated by injecting 10 ml of 30 mM hydrochloric acid. Injections of mIgG Fc-PDGFβR and each concentration of anti-PDGFβR DFM-PEG were repeated over the blank surface as controls. The sensorgram for each anti-PDGFβR DFM-PEG concentration was corrected with the corresponding sensorgram for the blank surface after deletion of the mIgG Fc-PDGFβR injection and regeneration step. Kinetic parameters were calculated using BIAevaluation 2.1 software.

Results for anti-PDGFβR DFM-PEG, both prepared from PEGylated Intermediate 4 (site-specific) and randomly derivatised anti-PDGFbR DFM-PEG are shown in Table 1. Unmodified DFM prepared with BMH as cross-linker and IgG were used to compare binding parameters. Binding affinity as quantified by the Kd value was similar between the IgG and unmodified DFM at $1.07 \times 10^{-10}$ M and $1.27 \times 10^{-10}$ M respectively. Random modification with PEG (1.3 per di-Fab') resulted in a substantial loss of binding affinity to $8.97 \times 10^{-10}$ M. Site-specific PEGylation with the same size PEG molecule resulted in much improved binding affinity with a Kd value of $2.10 \times 10^{-10}$ M.

TABLE 1

BIAcore analysis of DFM-PEG 40 kDa compared to IgG and unmodified DFM.

| Sample | kass | kdiss | Kd (M) |
|---|---|---|---|
| IgG | $9.74 \times 10^6$ | $1.04 \times 10^{-4}$ | $1.07 \times 10^{-10}$ |
| DFM | $1.81 \times 10^7$ | $2.29 \times 10^{-3}$ | $1.27 \times 10^{-10}$ |
| DFM-PEG 40 kDa (random) | $4.65 \times 10^6$ | $4.17 \times 10^{-3}$ | $8.97 \times 10^{-10}$ |
| DFM-PEG 40 kDa (site-specific) | $8.90 \times 10^6$ | $1.88 \times 10^{-3}$ | $2.10 \times 10^{-10}$ |

Pharmacokinetics

For pharmacokinetic analysis, samples were radiolabelled with $^{125}$I using Bolton-Hunter reagent by standard methodology and desalted into phosphate buffered saline at pH 6.8 to remove unreacted $^{125}$I. Groups of six male wistar rats were injected i.v. into the tail vein with 20 mg of labelled material. At selected time points, blood samples were taken, counted in a gamma counter, and the percent injected dose per gram of blood calculated. The clearance rates and area under the curve values were determined using the SIPHAR software package.

Figure 2:
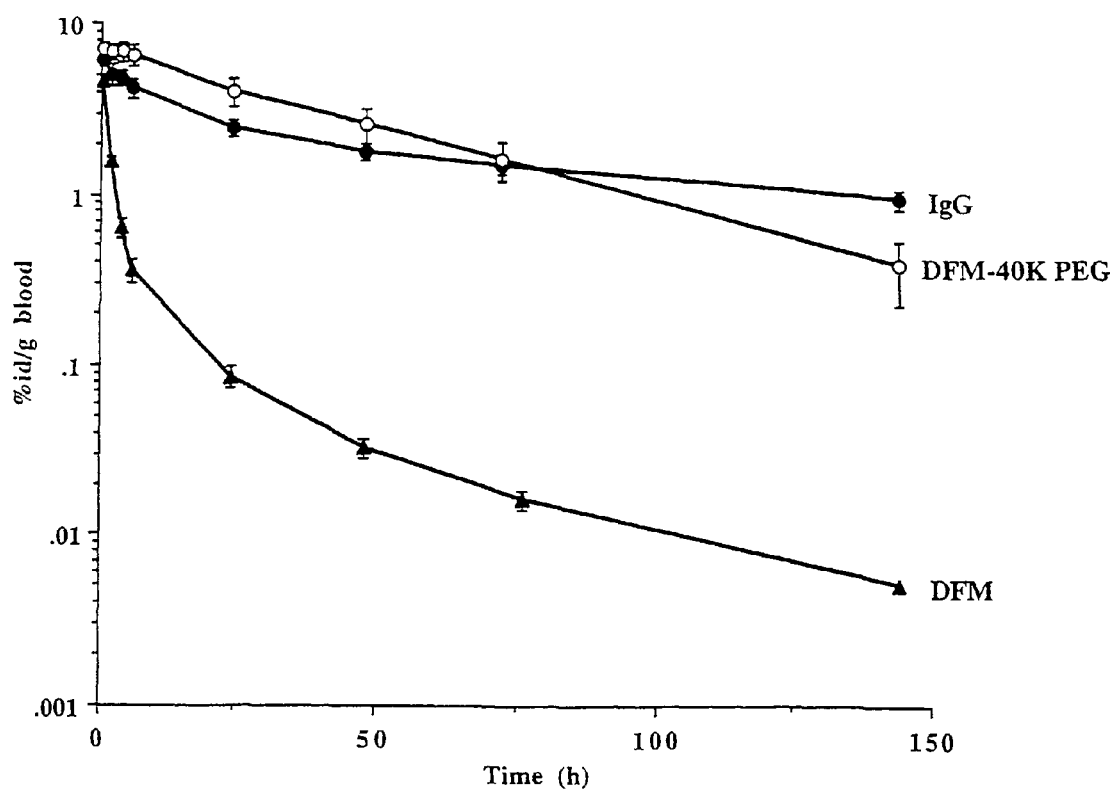
FIG. 2 Pharmacokinetics of $^{125}$I-labelled anti-PDGFβR DFM-PEG (40 kDa, site-specific) compared to DFM and IgG in rats.

Results (FIG. 2) demonstrated slower blood clearance for DFM-PEG conjugate compared to unmodified DFM. This was also reflected in the calculation of pharmacokinetic parameters. Pharmacokinetics of IgG and DFM were best fitted to a two compartment model, whereas DFM-PEG was best fitted to a single compartment model. Results demonstrated a significantly longer half-life and increased area-under-the-curve for DFM-PEG compared to DFM (Table 2).

TABLE 2

Pharmacokinetic parameters of anti-PDGFβR IgG, DFM and DFM-PEG (40 kDa) site-specific.

| | t½ α (hours) | t½ β (hours) | AUC (0–) (% dose × h) | AUC (% of IgG value) |
|---|---|---|---|---|
| IgG | 5.3 +/– 1.3 | 95.9 +/– 10.9 | 6442 +/– 525 | 100 |
| DFM | 0.86 +/– 0.1 | 28.7 +/– 11.6 | 283 +/– 71 | 4.4 |

TABLE 2-continued

Pharmacokinetic parameters of anti-PDGFβR IgG, DFM and DFM-PEG (40 kDa) site-specific.

| | t½ α (hours) | t½ β (hours) | AUC (0–) (% dose × h) | AUC (% of IgG value) |
|---|---|---|---|---|
| DFM-PEG (40 kDa) | — | 33.6 +/– 4.5 | 5318 +/– 1190 | 82 |

Bioassay

The potency of anti-PDGFβR DFM and DFM-PEG samples was tested by their ability to block 3H thymidine incorporation by SK-5 dermal fibroblasts in response to PDGF BB. SK-5 cells (grown in DMEM+10% heat inactivated fetal calf serum, 1% glutamine, !% sodium pyruvate and 0.025 M HEPES buffer) were trypsinised at 80% confluence and seeded at 5,000 cells/0.1 ml per well in a 96 well tissue culture plate, in serum-free media (1:1 DMEM:HAM's F12+5 ug/ml insulin, 16 ng/ml selenium, 20 ug/ml transferrin, 1 mg/ml bovine serum albumin, 1% glutamine, 0.025 M HEPES buffer and pen. strep.) Cells were placed in a 37°, 5% $CO_2$, 95% humidity, incubator for 24 h to quiesce. Media alone, antibody alone, PDGF BB at 10 ng/ml or 20 ng/ml final concentration, or PDGF BB together with varying concentrations of antibody were added to the wells, to a final volume of 0.2 ml. Between 5 and 10 wells were used for each condition. 6-8 h later, 3H thymidine (0.5 mCi per well) was added and cells left overnight. Plates were removed from the incubator and placed at −20° for 24 h in order to facilitate harvesting. Plates were thawed and DNA harvested onto filter mats using a Skatron Micro96 Harvester. Mats were dried at 67° for 90 min, Betaplate Scint (Wallac) added and mats counted in a LKB Wallac 1205 BETAPLATER liquid scintillation counter.

Figure 3:
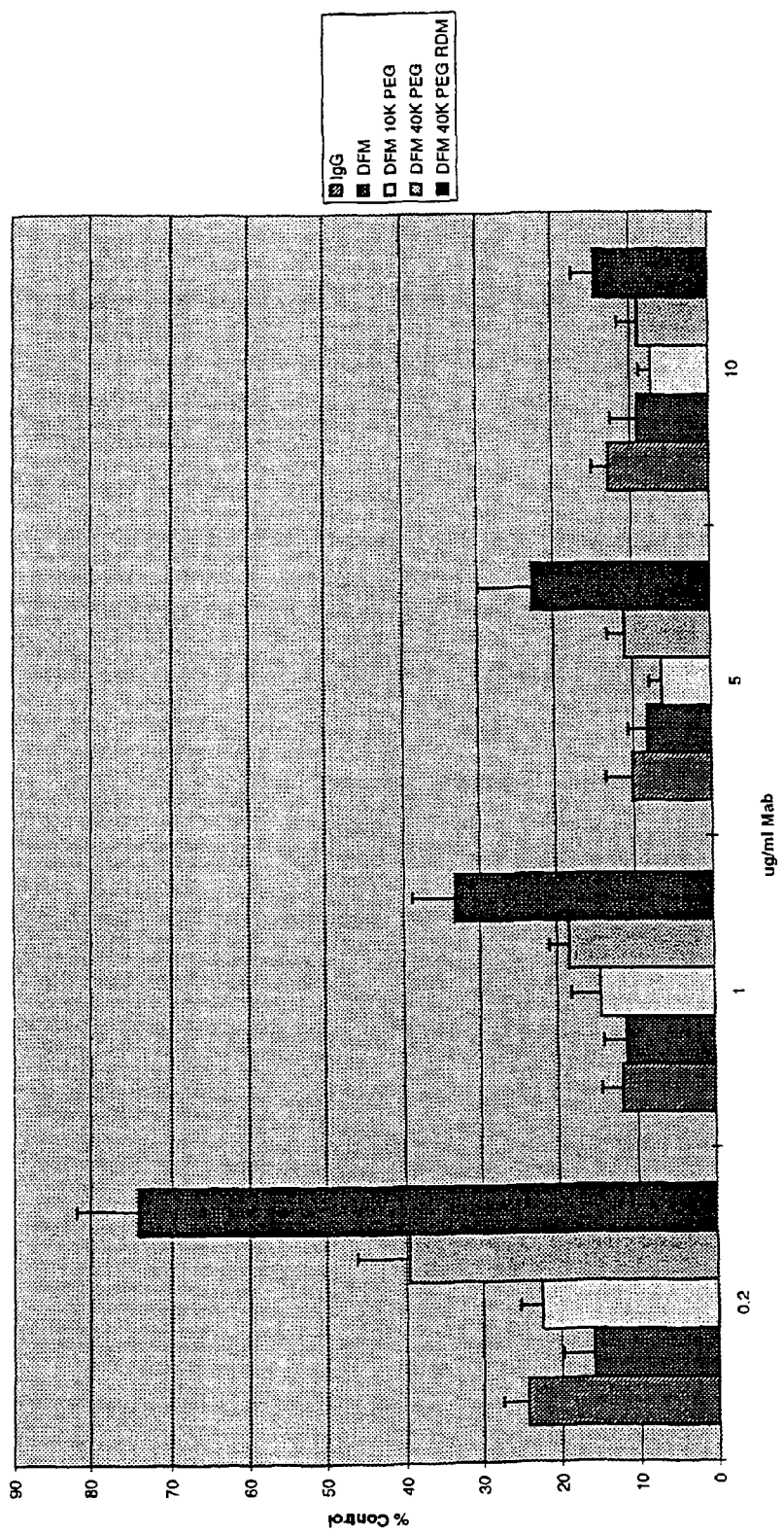
FIG. 3 Inhibition of SK-5 proliferation response to 10 ng/ml PDGF BB by anti-PDGFβR DFM-PEG (40 kDa random), DFM-PEG (40 kDa site-specific), DFM-PEG (10 kDa SS linker, site-specific), DFM and IgG.
Figure 4:
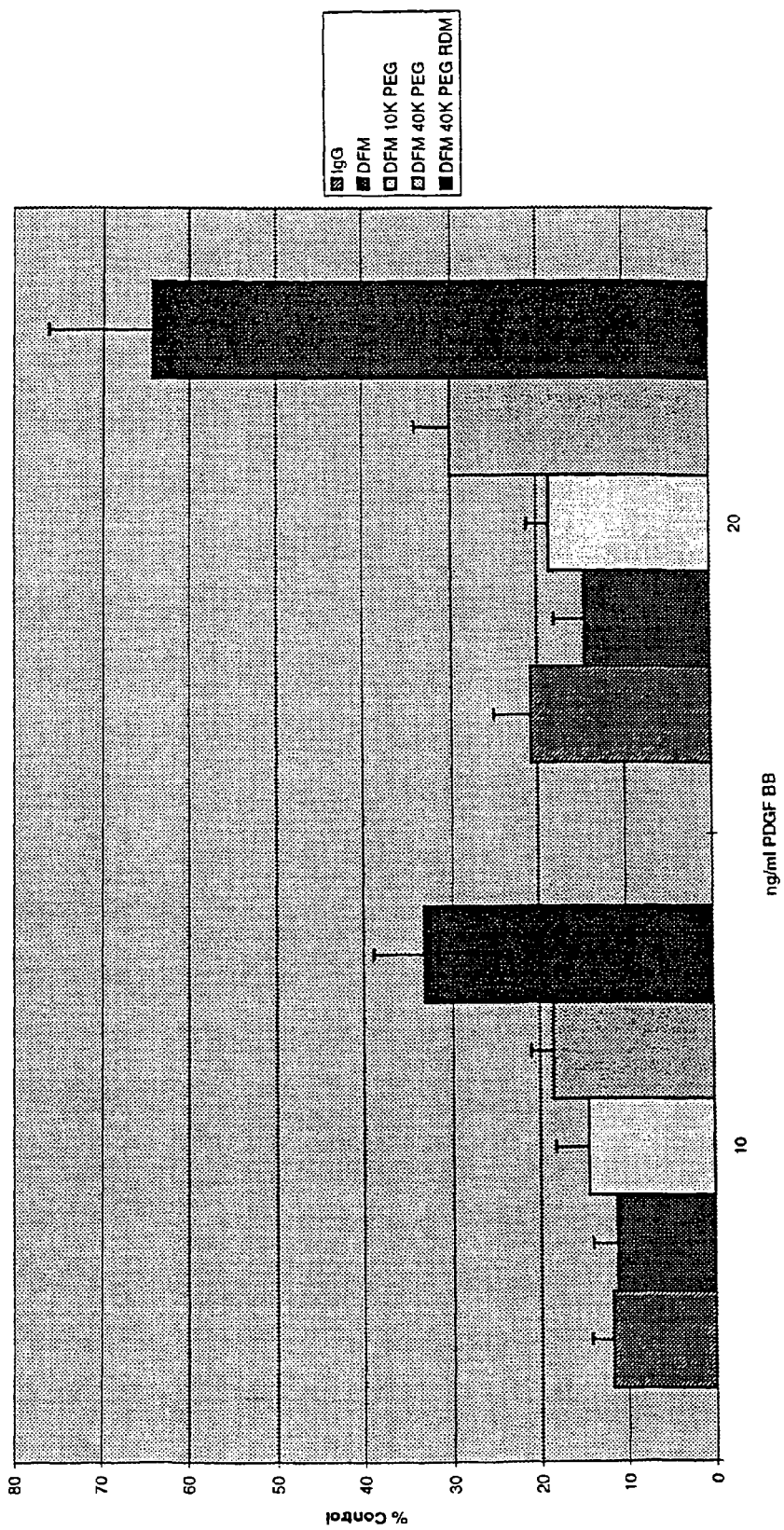
FIG. 4 Inhibition of SK-5 proliferation response to 10 ng/ml or 20 ng/ml PDGF BB by 1 microgram/ml of anti-PDGFβR DFM-PEG (40 kDa random), DFM-PEG (40 kDa site-specific), DFM-PEG (10 kDa SS linker, site-specific), DFM and IgG.

At 10 ng/ml PDGF BB, and 10 mg/ml of anti-PDGFβR DFM or DFM-PEG, incorporation of 3H thymidine is inhibited by 85-92% by all forms of the antibody. As the concentration of antibody is decreased, the difference between random PEG attachment and site-specific attachment becomes clear (FIG. 3). This is equally shown by increasing the concentration of PDGF BB to 20 ng/ml (FIG. 4). There is at least a two-fold decrease in potency between the randomly PEG modified 40 kDa DFM and the site-specific 40 kDa DFM.

EXAMPLE 2

Site-Specific Attachment of 10 kDa and 20 kDa PEG Succinimidyl Succinate Derivatives Intermediate 4 was derivatised with 20 kDa PEG-succinimidyl succinate (Polymer Labs), or 10 kDa PEG-succinimidyl succinate (Polymer Labs), and used to prepare anti-PDGFβR DFM-PEG as described in Example 1. In this case purification of the DFM-PEG conjugates was achieved using ion-exchange chromatography on Mono-S. Mono S chromatography was carried out using a column equilibrated with 50 mM acetate pH 4.5, after application of sample and washing with equilibration buffer, bound material was eluted using a linear gradient of sodium chloride. Following this step DFM-PEG was further purified using gel filtration on Sephacryl S-200 run in phosphate buffered saline diluted 1:1 with water. SDS-PAGE analysis revealed successful attachment of PEG had taken place (FIG. 1).

Analysis of antigen binding was carried out by BIAcore analysis as described in Example 1. Results shown in Table 3 demonstrate that these PEG derivatives can be attached with little loss in antigen binding affinity.

TABLE 3

BIAcore analysis of DFM-PEG prepared with succinimidyl succinate (SS) linkage.

| Sample | kass | kdiss | Kd (M) |
|---|---|---|---|
| DFM | $1.81 \times 10^7$ | $2.29 \times 10^{-3}$ | $1.27 \times 10^{-10}$ |
| DFM-PEG 10 kDa (SS linkage) | $1.53 \times 10^7$ | $2.18 \times 10^{-3}$ | $1.42 \times 10^{-10}$ |
| DFM-PEG 20 kDa (SS linkage) | $1.20 \times 10^6$ | $2.06 \times 10^{-3}$ | $1.73 \times 10^{-10}$ |

Figure 5:
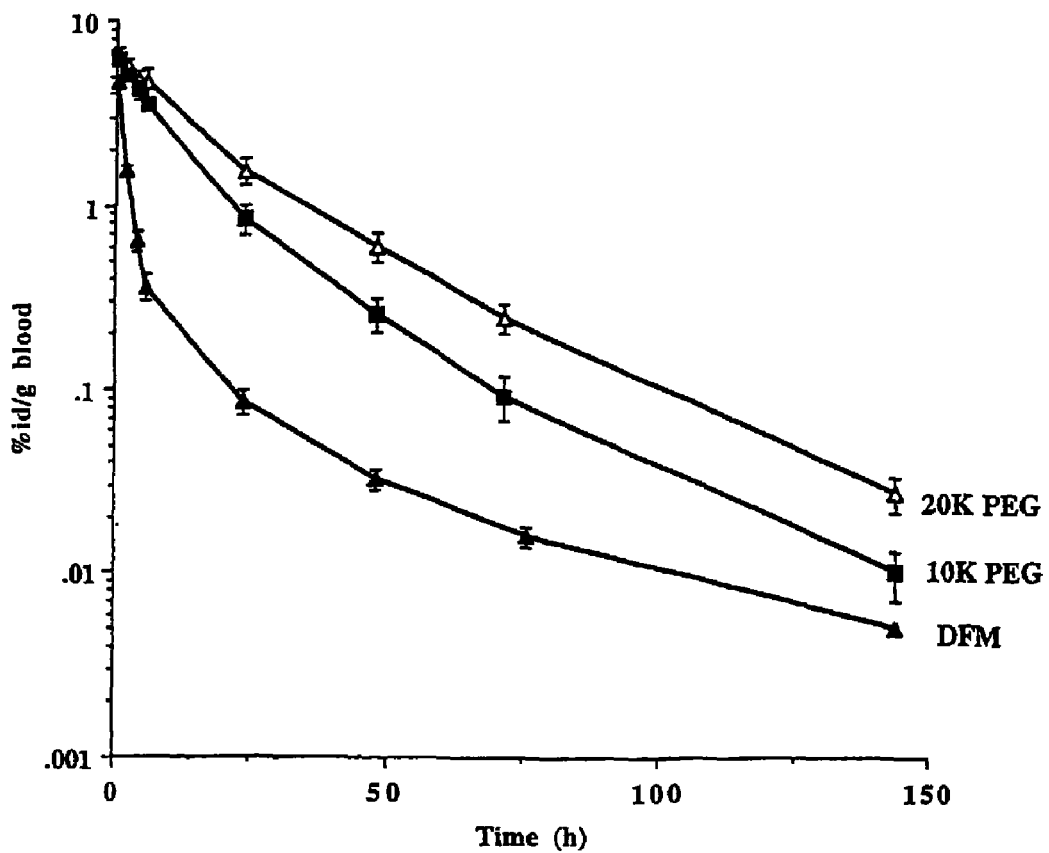
FIG. 5 Pharmacokinetics of $^{125}$I-labelled anti-PDGFβR DFM-PEG (10 kDa, SS linker) and DFM-PEG (20 kDa, SS linker) compared to DFM in rats.

These DFM-PEG conjugates were then examined in a pharmacokinetic study in rats using the method described in Example 1. Results (FIG. 5) demonstrate significantly slower blood clearance, (longer in vivo half-life) for the DFM-PEG conjugates compared to unmodified DFM.

EXAMPLE 3

Preparation of DFM-PEG Conjugates using 5 KDa PEG-SCM, 20 KDa PEG-SPA, 10K PEG2-NHS and 20K PEG2-NHS Derivatives Intermediate 4 was derivatised with 20 kDa PEG-succinimidyl propionate (Shearwater Polymers Inc.ibid), or 5 kDa PEG-succinimidyl ester of carboxy-methylated PEG (Shearwater Polymers Inc.), or 10 KDa PEG2-succinimide (2×5 KDa, Polymer Labs) or 20 KDa PEG2-succinimide (2×10 KDa, Polymer Labs), and used to prepare anti-PDGFβR DFM-PEG conjugates as described in Examples 1 & 2. These DFM-PEG derivatives were purified using ion-exchange chromatography followed by gel filtration as described in Example 2. SDS-PAGE analysis revealed that conjugation to PEG was successful in all cases. (FIG. 6). BIAcore analysis was also carried out to determine antigen binding affinity. Results shown in Table 4 demonstrate that these PEG derivatives can be attached with little loss in antigen binding affinity.

TABLE 4

BIAcore analysis of DFM-PEG derivatives

| Sample | kass | kdiss | Kd (M) |
|---|---|---|---|
| DFM | $1.81 \times 10^7$ | $2.29 \times 10^{-3}$ | $1.27 \times 10^{-10}$ |
| DFM-PEG 5 kDa (SCM linkage) | $1.89 \times 10^7$ | $2.58 \times 10^{-3}$ | $1.37 \times 10^{-10}$ |
| DFM-PEG 20 kDa (SPA linkage) | $9.80 \times 10^6$ | $2.37 \times 10^{-3}$ | $2.42 \times 10^{-10}$ |
| DFM-PEG 10 kDa (5 kDA × 2, NHS linkage) | $1.56 \times 10^7$ | $2.14 \times 10^{-3}$ | $1.38 \times 10^{-10}$ |
| DFM-PEG2 20 kDa (10 kDa × 2, NHS linkage) | $1.11 \times 10^7$ | $2.20 \times 10^{-3}$ | $1.99 \times 10^{-10}$ |

These DFM-PEG conjugates were then examined in a pharmacokinetic study in rats using the method described in Example 1. Results (FIG. 7) demonstrate significantly slower blood clearance, (longer in vivo half-life) for the DFM-PEG conjugates compared to unmodified DFM.

EXAMPLE 4

Preparation of Fab' hTNF40 Fab' (recognising human TNFα) was expressed in E. coli W3110 cells grown in a 10 liter fermenter. The Fab' fragment has a single cysteine residue present in its hinge region available for cross-linking. A cell extract was prepared as described in Example 1. The cell extract was diluted to a conductivity of 3.5 mS/cm, adjusted to pH4.5, and applied to a column of Streamline™ SP (Pharmacia) equilibrated with 50 mM acetate buffer pH4.5. After washing with equilibration buffer, the Fab' was eluted with 200 mM sodium chloride in 50 mM acetate buffer pH4.5. The pH of the eluted material was adjusted to 7.5 with 2M Tris, and was applied to a column of protein G Sepharose equilibrated with PBS. After washing with PBS, the Fab' was eluted with 0.1M glycine-hydrochloric acid pH2.7, and immediately the pH was re-adjusted to 6. The purified Fab' was then diafiltered into 0.1M phosphate buffer pH6 containing 2 mM EDTA.

Preparation of hTNF40 DFM-PEG (40 kDa, Site-Specific)

The hinge thiol group of the Fab' was activated by reduction with 11-mercaptoethylamine as described in Example 1. The sample was then desalted into 0.1M phosphate pH6 containing 2 mM EDTA. The number of thiol groups per Fab' molecule was measured as described in Example 1. The Fab' was cross-linked with the PEGylated cross-linker prepared from Intermediate 4 (40 kDa PEG bis-maleimide, Shearwater Polymers Inc., Huntsville, Ala., USA), at a 2.2:1 Fab':linker ratio at ambient temperature.

Figure 8:
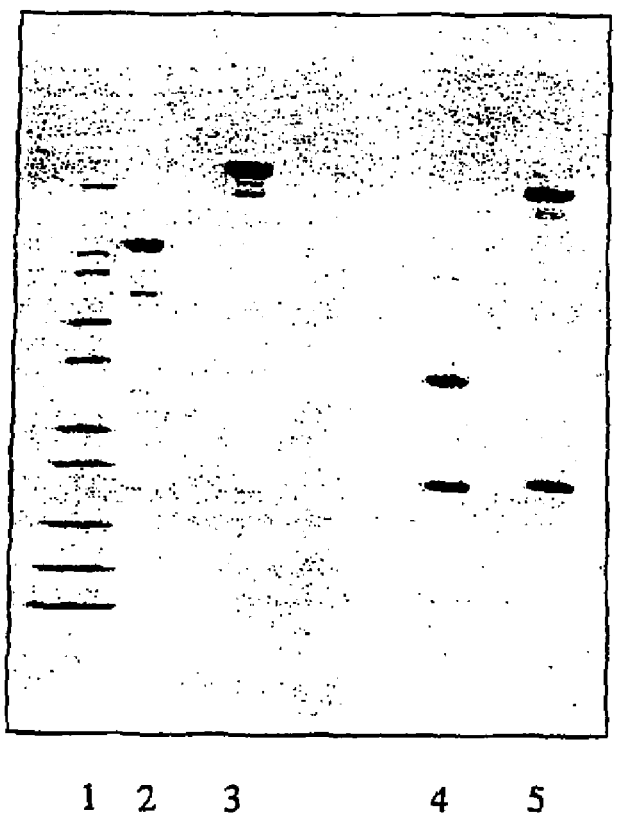
FIG. 8 SDS-PAGE analysis under non-reducing (lanes 2-3) and reducing (lanes 4-5) conditions.

The desired DFM-PEG was purified by gel filtration chromatography using Sephacryl S-200 HR (to remove unreacted Fab' and DFM) in 50 mM acetate buffer pH4.5, followed by cation exchange chromatography using SP Sepharose HP to separate DFM-PEG from Fab'-PEG. SP Sepharose HP chromatography was carried out using a column equilibrated with 50 mM acetate buffer pH4.5. After application of the sample and washing with equilibration buffer, bound material was eluted with a linear gradient of sodium chloride. Purified material was examined on SDS-PAGE and shown to have a slower mobility than unmodified DFM demonstrating successful conjugation of PEG (FIG. 8).

Antigen binding analysis by BIAcore

Antigen binding activity was assessed by BIAcore assay which measured affinity for TNF binding. Fab', DFM, IgG or PEG-DFM were captured with an immobilized anti-Fab' antibody, and human TNF passed over the surface. The kinetics of TNF binding were then analysed. Results from this analysis are shown in Table 5. Unmodified DFM prepared with BMH as cross-linker and IgG were used to compare binding parameters. Binding affinity as quantified by the Kd value was similar between IgG and DFM ($1.79 \times 10^{-10}$M and $1.07 \times 10^{-10}$M respectively). Site-specific PEGylation of DFM resulted in an almost identical binding affinity of $1.82 \times 10^{-10}$M, suggesting no loss of antigen binding function after PEG modification.

TABLE 5

BIAcore analysis of DFM-PEG 40 kDa compared to IgG, Fab' and unmodified DFM.

| Sample | kass | kdiss | Kd (M) |
|---|---|---|---|
| IgG | $4.21 \times 10^5$ | $7.54 \times 10^{-5}$ | $1.79 \times 10^{-10}$ |
| DFM | $2.97 \times 10^5$ | $3.17 \times 10^{-5}$ | $1.07 \times 10^{-10}$ |
| DFM-PEG 40 kDa (site-specific) | $3.31 \times 10^5$ | $6.02 \times 10^{-5}$ | $1.82 \times 10^{-10}$ |

Pharmacokinetics

For pharmacokinetic analysis, these samples were studied in rats using the method described in Example 1. The clearance rates and Auc values were determined using either the SIPHAR or WINNONLIN software packages.

Figure 9:
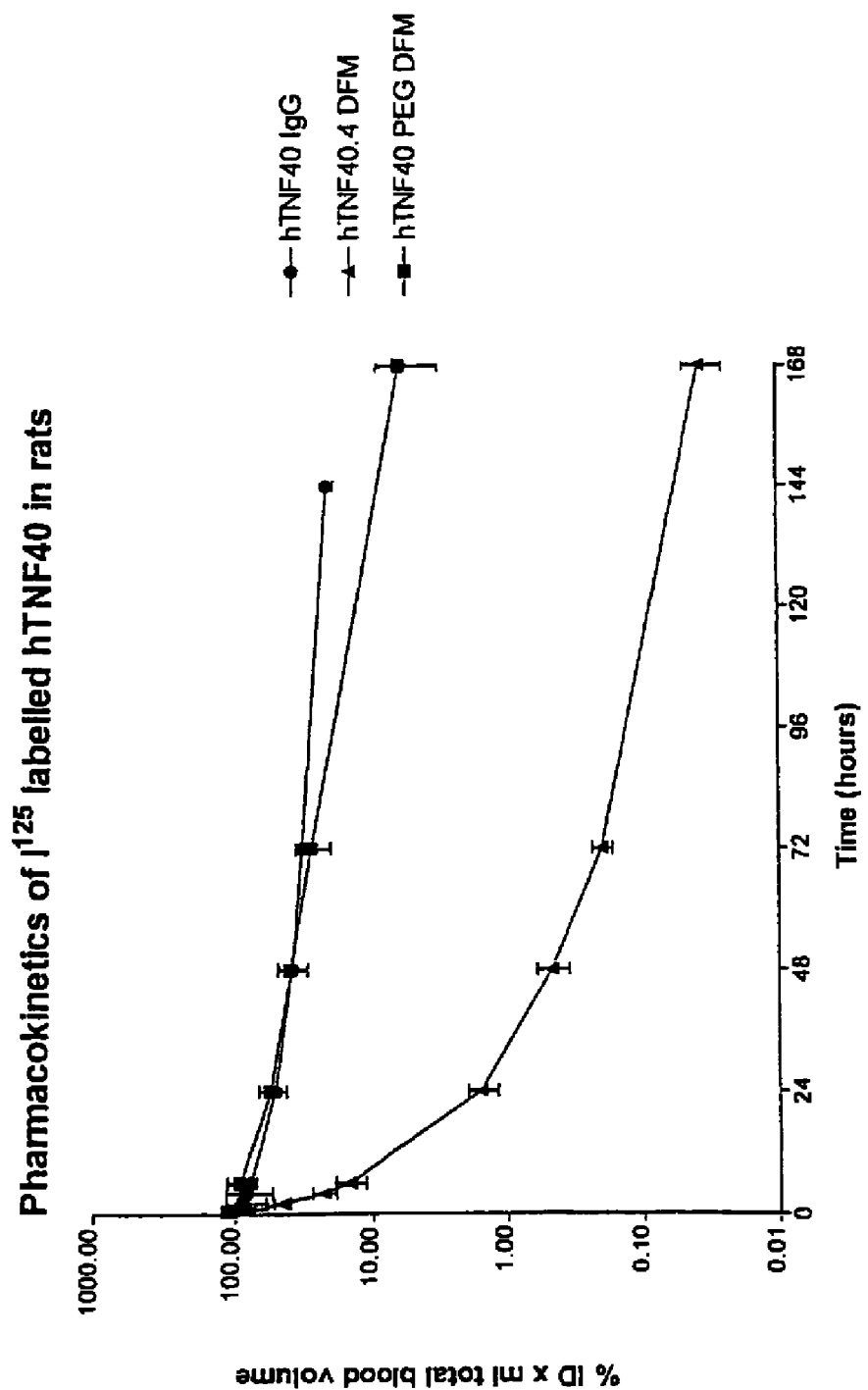
FIG. 9 Pharmacokinetics of $^{125}$I-labelled hTNF40 DFM-PEG (40 kDa, site-specific) compared to DFM and IgG in rats.

Results (FIG. 9) demonstrated significantly slower blood clearance (longer in vivo half-life) for the DFM-PEG conjugate compared to unmodified DFM. This was also reflected in the calculation of pharmacokinetic parameters, fitted using a two compartment model. The results demonstrated a significantly longer half-life and increased area under the curve for DFM-PEG compared to DFM (Table 6).

TABLE 6

Pharmacokinetic parameters of hTNF40 IgG, DFM and DFM-PEG (40 kDa) site specific.

| | t½ (hours) | t½ β (hours) | AUC (0−) (% dose × h) | AUC (% of IgG value) |
|---|---|---|---|---|
| IgG | 5.81 | 104.0 | 8791 | 100 |
| DFM | 1.50 | 11.1 | 390 | 4.4 |
| DFM-PEG (40 kDa) | — | 39.6 | 5235 | 59.5 |

The invention claimed is:

1. A divalent antibody fragment comprising two antibody heavy chains and at least one polymer molecule effective for increasing the circulating half-life of said fragment in covalent linkage, each heavy chain being covalently linked to the other by at least one non-disulphide interchain bridge linking the sulphur atom of a cysteine residue in one chain to the sulphur atom of a cysteine residue in the other chain, said cysteine residues being located outside of the variable region domain of each chain, characterised in that the at least one covalently linked polymer molecule is covalently attached to the at least one non-disulphide interchain bridge.

2. An antibody fragment according to claim 1 in which each heavy chain is covalently linked to the other by a single non-disulphide bridge, said bridge having attached thereto a covalently linked polymer molecule effective for increasing the circulating half-life of said fragment.

3. An antibody fragment according to claim 1 wherein each heavy chain is paired with a light chain.

4. An antibody fragment according to claim 1 wherein each heavy chain is a $V_H$-CH1 chain terminally substituted by a hinge region domain.

5. An antibody fragment according to claim 4 wherein each non-disulphide bridge present links the sulphur atom of a cysteine residue located in the hinge region domain of one heavy chain, to the sulphur atom of a cysteine residue in the hinge region domain of the other chain.

6. An antibody fragment according to claim 1 wherein the polymer is an optionally substituted straight or branched chain polymer selected from the group consisting of polyalkylene, polyalkenylene and polyoxyalkylene, or a branched or unbranched polysaccharide.

7. An antibody fragment according to claim 6 wherein the polymer is an optionally substituted straight or branched chain polymer selected from the group consisting of poly (ethylene glycol) or a derivative of poly(ethylene glycol).

8. An antibody fragment according to claim 7 wherein the polymer is selected from the group consisting of methoxy (polyethylene glycol) or a derivative of methoxy(polyethylene glycol).

9. An antibody fragment according to claim 8 wherein the polymer has a molecular weight in the range from about 25000 Da to about 40000 Da.

10. An antibody fragment according to claim 1 wherein each interchain bridge is the residue of a homo- or heterobifunctional cross-linking reagent.

11. An antibody fragment according to claim 10 wherein each bridge is an optionally substituted $C_{4-20}$ alkylene chain optionally interrupted by one or more heteroatoms or heteroatom-containing groups.

12. An antibody fragment according to claim 1 which is covalently attached to one or more effector or reporter molecules.

13. An antibody fragment according to claim 1 which is able to selectively bind to a cell surface or soluble antigen.

14. An antibody fragment according to claim 13 wherein the antigen is human tumour necrosis factor-α or a platelet derived growth factor or a receptor thereof.

15. A pharmaceutical composition comprising an antibody fragment according to any of the preceding claims together with one or more pharmaceutically acceptable excipients, diluents or carriers.

* * * * *